US012758666B2

(12) United States Patent
Hibner et al.

(10) Patent No.: US 12,758,666 B2
(45) Date of Patent: Oct. 13, 2026

(54) FLUSHING SYSTEMS FOR SURGICAL INSTRUMENTS

(71) Applicant: CILAG GMBH INTERNATIONAL, Zug (CH)

(72) Inventors: John A. Hibner, Mason, OH (US); Daniel Mumaw, Liberty Township, OH (US); Janna B. Volz, West Chester, OH (US); Clinton W. Denlinger, Cincinnati, OH (US); Robert M. Householder, Norwood, OH (US); Julie A. Hoover, Sardinia, OH (US); Joseph M Nath, West Chester, OH (US); Nicholas Seipelt, Cincinnati, OH (US); Konstantin G. Zabotkin, Mason, OH (US); Scott D. Harrington, Mason, OH (US); Reid Butler, Chicago, IL (US)

(73) Assignee: CILAG GMBH INTERNATIONAL, Zug (CH)

( * ) Notice: Subject to any disclaimer, the term of this patent is extended or adjusted under 35 U.S.C. 154(b) by 384 days.

(21) Appl. No.: 18/531,554

(22) Filed: Dec. 6, 2023

(65) Prior Publication Data

US 2025/0186640 A1 Jun. 12, 2025

(51) Int. Cl.

| | |
|---|---|
| ***A61L 2/18*** | (2026.01) |
| ***A61L 2/26*** | (2006.01) |
| *A61L 103/15* | (2026.01) |

(52) U.S. Cl.
CPC .................. *A61L 2/18* (2013.01); *A61L 2/26* (2013.01); *A61L 2103/15* (2026.01); *A61L 2202/123* (2013.01); *A61L 2202/17* (2013.01)

(58) Field of Classification Search
CPC .......... A61L 2/18; A61L 2/26; A61L 2103/15; A61L 2202/123; A61L 2202/17
See application file for complete search history.

(56) References Cited

U.S. PATENT DOCUMENTS

2008/0200765 A1* 8/2008 Mondschein ........ A61B 1/3132 600/157
2013/0186428 A1* 7/2013 Lutz ....................... A61B 90/70 134/1
2014/0121661 A1* 5/2014 Schmaltz ........... A61B 18/1445 606/41
2021/0068890 A1* 3/2021 Baril .............. A61B 17/320092

* cited by examiner

*Primary Examiner* — Maris R Kessel
*Assistant Examiner* — Aham Lee
(74) *Attorney, Agent, or Firm* — Vorys, Sater, Seymour and Pease LLP

(57) ABSTRACT

A surgical tool includes a drive housing, a shaft extending distally from the drive housing, a distal seal arranged at a distal end of the shaft, and a flush tube extending from the drive housing within the shaft and terminating proximal to the distal seal. A flushing fluid conveyed distally through the flush tube is discharged from the flush tube and impinges upon the distal seal. A proximal drain is arranged within the drive housing and in fluid communication with an annulus defined between the flush tube and an inner wall of the shaft. The flushing fluid discharged from the flush tube circulates proximally within the annulus to the proximal drain to be discharged from the drive housing.

14 Claims, 10 Drawing Sheets

FLUSHING SYSTEMS FOR SURGICAL INSTRUMENTS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Reusable MIS instruments need to be cleaned and sanitized following operation and prior to being put back into service. One way to clean MIS instruments is by flushing the interior of the surgical instrument with a flushing fluid. The flushing fluid is typically introduced into the drive housing of the instrument and conveyed into a flush tube that extends distally within a shaft extending from the drive housing. The flushing fluid is eventually discharged from the flush tube at or near a wrist and end effector of the instrument, following which the flushing fluid makes an abrupt 180° turn and flows back up the shaft within an annulus defined between the outer diameter of the flush tube and the inner diameter of the shaft. The turbulent flow and pressure of the flushing fluid flushes out debris and bioburden that may be present within the shaft, near the wrist, and within the drive housing.

The flushing fluid returning to the drive housing can be circulated generally into the interior of the drive housing to flush cleanse and disinfect the various internal component parts and mechanisms housed within the drive housing. The flushing fluid can then naturally (or under pressure) drain out of the drive housing via various apertures, holes, and flush ports defined in the drive housing. The debris and bioburden entrained within the flushing fluid, however, can become lodged within the drive housing, which is undesirable.

Moreover, some flushing systems targeted at a distal seal located at or near the wrist create non-turbulent flow as the flushing fluid turns from flowing distal to proximal. This non-turbulent flow may not be sufficient to clean the areas consistently, thus potentially leaving soil or requiring longer cleaning procedures or multiplying steps required in cleaning procedures.

What is needed is a means of more effectively conveying and draining the flushing fluid from the drive housing to reduce or entirely eliminate the introduction of bioburden and debris into the proximal end of the instrument.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical tools and, more particularly, to a flushing system that includes a proximal drain arranged within the drive housing of the surgical tool to receive and discharge flushing fluid entrained with debris and bioburden.

Embodiments discussed herein describe a surgical tool that includes a drive housing, a shaft extending distally from the drive housing, a distal seal arranged at a distal end of the shaft, and a flush tube extending from the drive housing within the shaft and terminating proximal to the distal seal. A flushing fluid conveyed distally through the flush tube is discharged from the flush tube and impinges upon the distal seal to remove debris and bioburden. A proximal drain is arranged within the drive housing and in fluid communication with an annulus defined between the flush tube and an inner wall of the shaft. The flushing fluid discharged from the flush tube and entrained with the debris and bioburden circulates proximally within the annulus to the proximal drain to be discharged from the drive housing.

Figure 1:
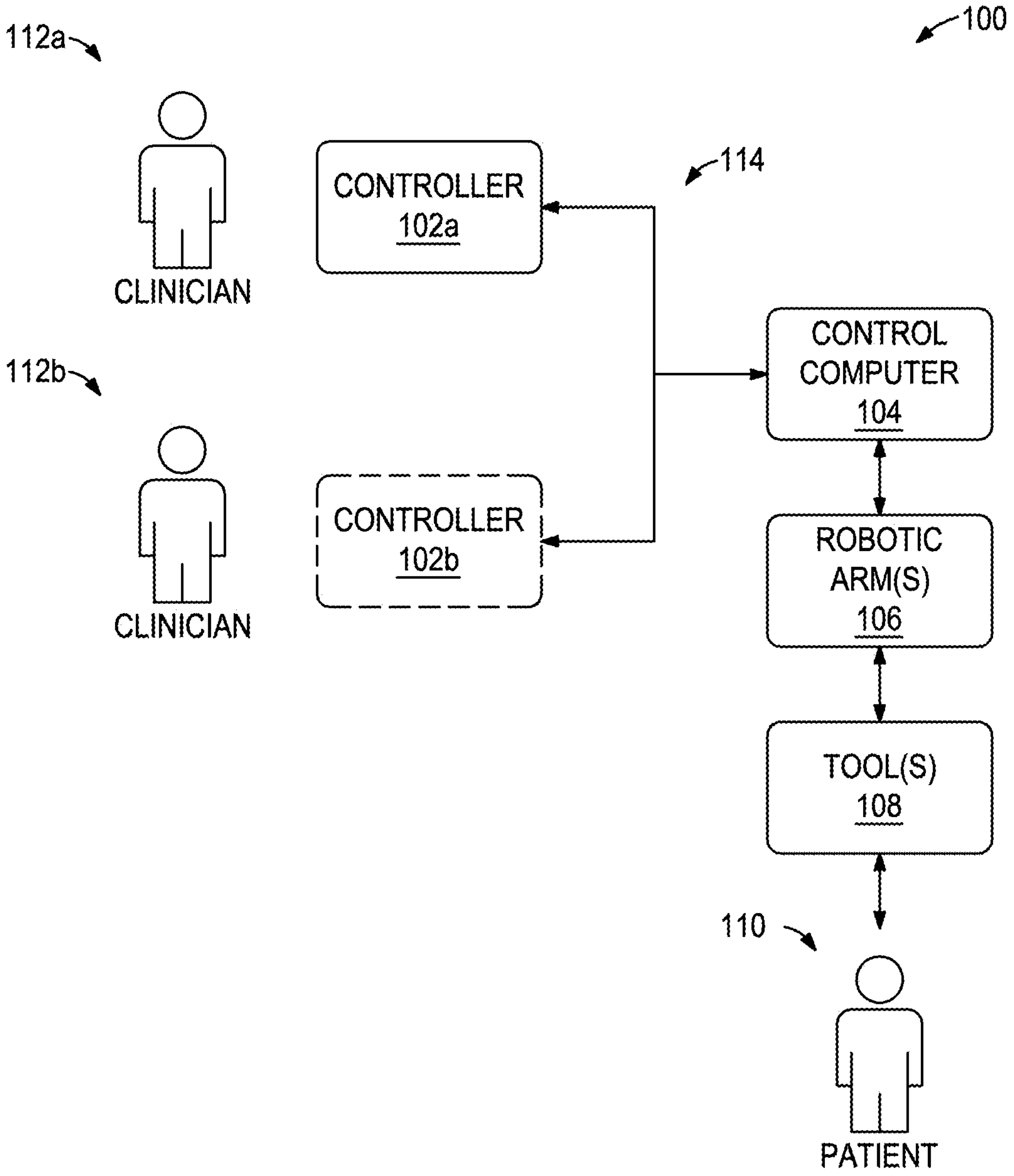
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
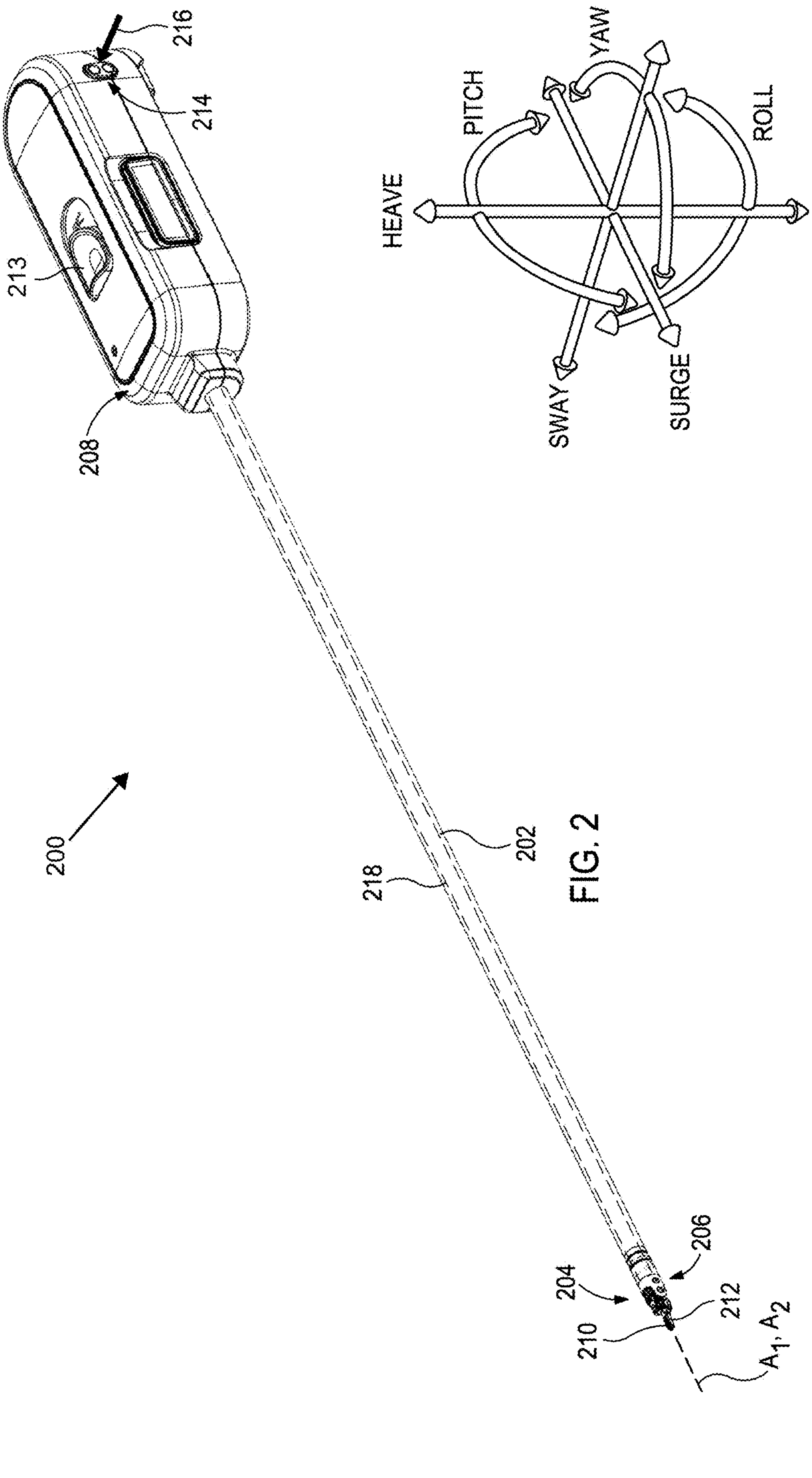
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a needle driver that includes opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a tissue grasper, a vessel sealer, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

The surgical tool 200 may further include a manual release switch 213 that may be manually actuated by a user (e.g., a surgeon) to override the cable driven system and thereby manually operate the end effector 204. The release switch 213 is movably positioned on the drive housing 208, and a user is able to manually move (slide) the release switch 213 from a disengaged position, as shown, to an engaged position. In the disengaged position, the surgical tool 200 is able to operate as normal. As the release switch 213 moves to the engaged position, however, various internal component parts of the drive housing 208 are simultaneously moved, thereby resulting in the jaws 210, 212 opening, which might prove beneficial for a variety of reasons. In some applications, for example, the release switch 213 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 213 may be actuated (enabled) to open the jaws 210, 212 in preparation for cleaning and/or sterilization of the surgical tool 200.

The surgical tool 200 may further include one or more flush ports 214 (two shown) provided on the drive housing 208 and providing a means to introduce a cleaning or flushing fluid 216 into the surgical tool 200 during a cleaning and sterilization process. The flushing fluid 216 may comprise, for example, sterile water, saline, a mixture of water and various cleaning agents, or any combination thereof. The flushing fluid 216 may be introduced into the drive housing 208 via the flush port 214, and suitable conduits and plumbing within the drive housing 208 convey the flushing fluid 216 into a flush tube 218 (shown in dashed lines) extending distally within the shaft 202. The flushing fluid 216 circulates (distally) through the flush tube 218 and then flows back up the shaft 202 (proximally) to the drive housing 208. In some applications, the flushing fluid 216 is discharged from the flush tube 218 at or near the wrist 206 where it makes an abrupt 180° turn and flows back up the shaft 202 (proximally) within an annulus defined between the outer diameter of the flush tube 218 and the inner diameter of the shaft 202. In such applications, the turbulent flow and pressure of the flushing fluid 216 flushes out debris and bioburden that may be present within the shaft 202, near the wrist 206, and within the drive housing 208.

In some applications, the flushing fluid 216 returning to the drive housing 208 may then be circulated back to secondary or tertiary flush ports (a discharge port) and thereby discharged from the drive housing 208. In other applications, the flushing fluid 216 may be circulated generally into the interior of the drive housing 208 to flush, cleanse, and disinfect the various internal component parts and mechanisms housed within the drive housing 208. In such applications, the flushing fluid 216 may then naturally (or under pressure) drain out of the drive housing 208 via various apertures, holes, and flush ports defined in the bottom of the drive housing 208. Moreover, in such applications, the debris and bioburden entrained within the flushing fluid 216 may become lodged and otherwise remain within the drive housing 208 following draining, which is undesirable since it could cause damage to the internal component parts of the drive housing 208.

According to embodiments of the present disclosure, the surgical tool 200 may include a proximal drain (not shown) mounted within the drive housing 208 and in fluid communication with the return path of the flushing fluid 216 such that the flushing fluid 216 returning to the drive housing 208 from the distal end of the shaft 202 will substantially or entirely flow out of the drive housing 208 via the proximal drain. Including the proximal drain in the surgical tool 200 may help reduce or entirely eliminate the introduction of bioburden and debris into the proximal end of the surgical tool 200 (e.g., within the drive housing 208). The proximal drain may also eliminate the need for lower flush ports in the drive housing 208, and further eliminate the need for a check valve within the conduit extending from the flush port 214 to prevent backflow of the flushing fluid 216.

Figure 4:
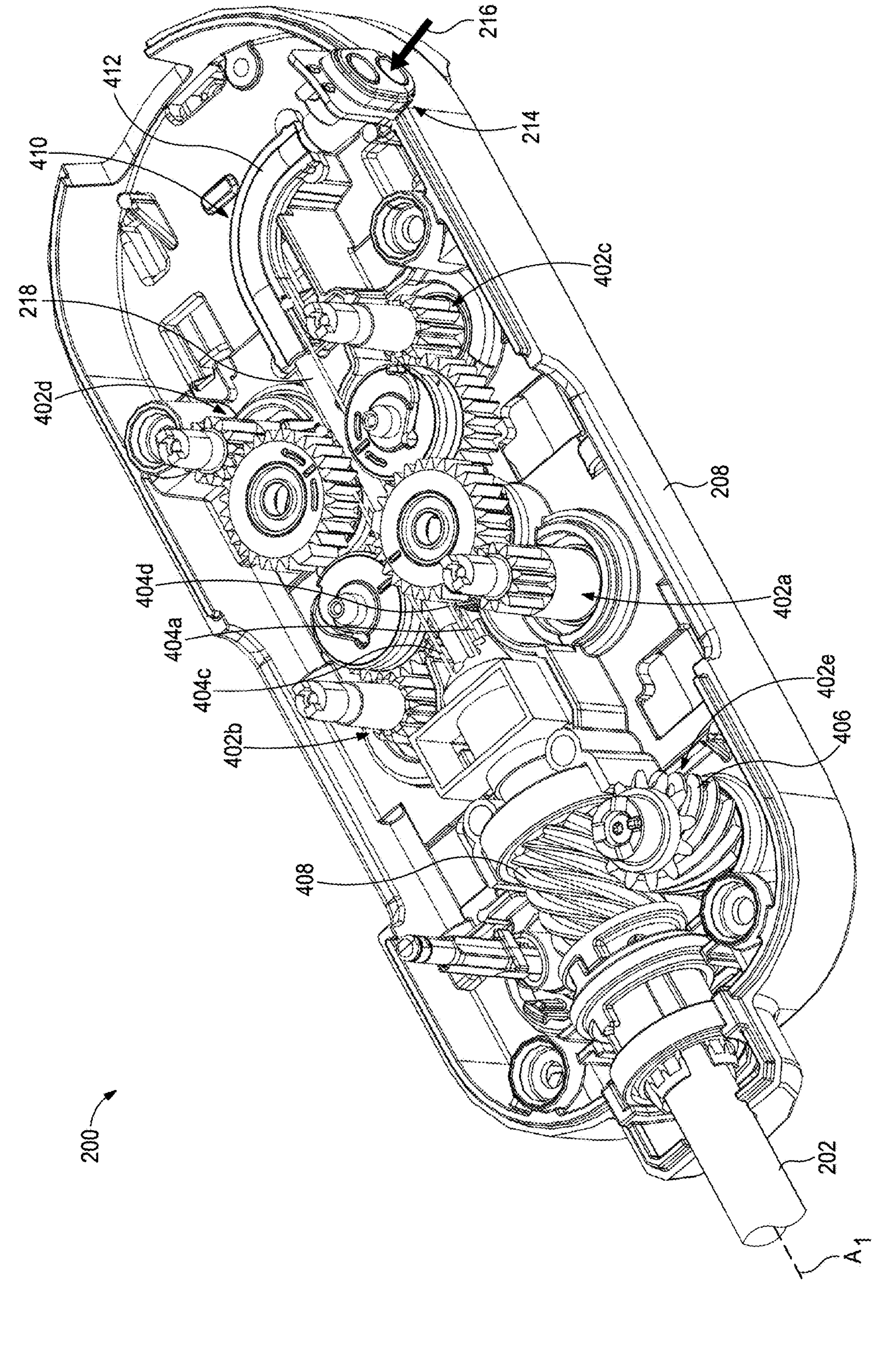
FIG. 4 is an exposed isometric view of the interior of the drive housing, according to one or more embodiments.

FIG. 4 is an exposed isometric view of the interior of the drive housing 208, according to one or more embodiments. Several component parts that would otherwise be contained within the drive housing 208 are not depicted in FIG. 4 to enable discussion of the depicted component parts. As illustrated, the drive housing 208 houses and otherwise contains a plurality of capstan assemblies operable to operate surgical tool 200 (FIG. 2). In particular, the drive housing 208 may contain or house first, second, third and fourth capstan assemblies 402*a*, 402*b*, 402*c*, and 402*d*. The capstan assemblies 402*a-d* may be alternately referred to as "drive cable" capstan assemblies since they are operable to actuate a plurality of drive cables shown as drive cables 404*a*, 404*b* (occluded), 404*c*, and 404*d*, which extend from the corresponding capstan assembly 402*a-d* and into the shaft 202. The drive cables 404*a-d* through the wrist 206 (FIG. 2) and terminate at the end effector 204 (FIG. 2).

The drive cables 404*a-d* may form part of the cable driven motion system briefly mentioned above, and may comprise cables, bands, lines, cords, wires, woven wires, ropes, strings, twisted strings, elongate members, belts, shafts, flexible shafts, drive rods, or any combination thereof. The drive cables 404*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof.

As illustrated, each capstan assembly 402*a-d* may include various actuation means (e.g., capstan shafts, gears, pulleys, etc.) operable to act on an associated drive cable 404*a-d* upon actuation. Description of the mechanics and operation of the capstan assemblies 402*a-d* is outside the scope of this disclosure and therefore will not be described herein. Selective actuation of the capstan assemblies 402*a-d* applies tension (i.e., pull force) to the given drive cable 404*a-d* in the proximal direction, which urges the drive cable 404*a-d* to translate longitudinally within the shaft 202. Selective and antagonistic operation of the drive cables 404*a-d* can open or close the jaws 210, 212 (FIG. 2), or may cause the end effector 204 to articulate at the wrist 206.

The drive housing 208 may further contain or house a fifth capstan assembly 402*e*, which may include a drive gear 406 configured to mesh and interact with a driven gear 408 operatively coupled to the shaft 202 within the drive housing 208 such that rotation of the driven gear 408 correspondingly rotates the shaft 202. In the illustrated embodiment, the drive and driven gears 406, 408 comprise intermeshed helical gears, and actuation of the fifth capstan assembly 402*e* will correspondingly control rotation of the shaft 202 about the longitudinal axis $A_1$.

The surgical tool 200 may further contain or house a flushing system 410 operable to clean and flush debris and bioburden from certain parts of the surgical tool 200 during cleaning and sterilization processes. The flushing system 410 may include the flush port 214 and the flush tube 218. As illustrated, the flushing system 410 may further include a transition conduit 412 that extends from the flush port 214, and the flush tube 218 extends through the transition conduit to be fluidly coupled to the flush port 214. In other embodiments, however, the transition conduit 412 may be omitted and the flush tube 218 may be bent or otherwise configured to fluidly couple directly to the flush port 214, without departing from the scope of the disclosure. The flushing fluid 216 may be introduced to the drive housing 208 at the flush port 214 under pressure and conveyed to the flush tube 218. As briefly mentioned above, the flushing fluid 216 may then be circulated through the flush tube 218, which extends within the shaft 202, and is eventually discharged from the flush tube 218 at or near the wrist 206 (FIG. 2).

Figure 5A:
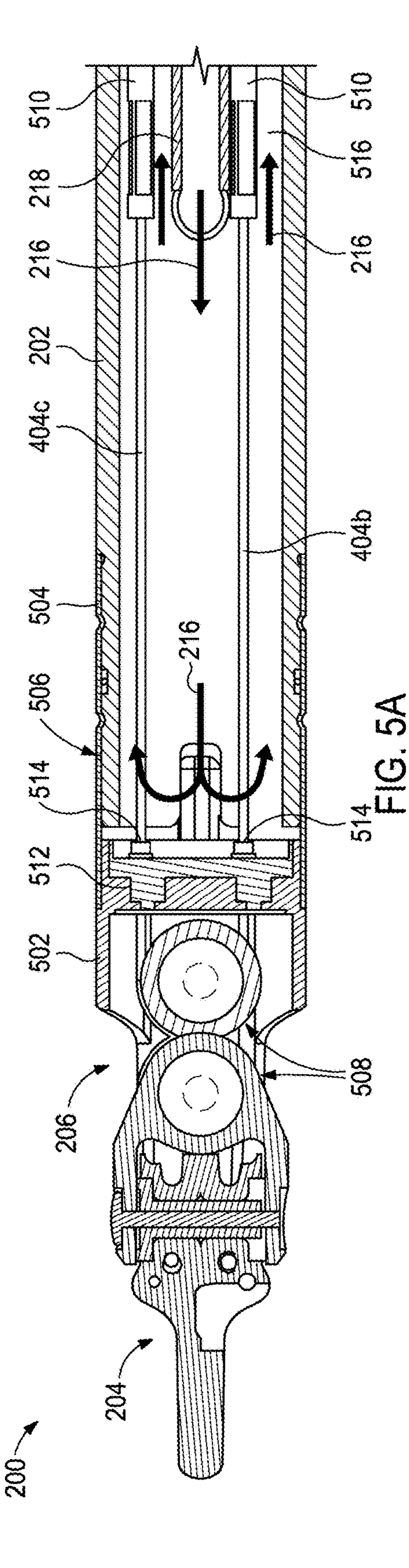
FIGS. 5A and 5B are cross-sectional and isometric views, respectively, of the distal end of the surgical tool of FIG. 2, according to one or more embodiments of the present disclosure.
Figure 5B:
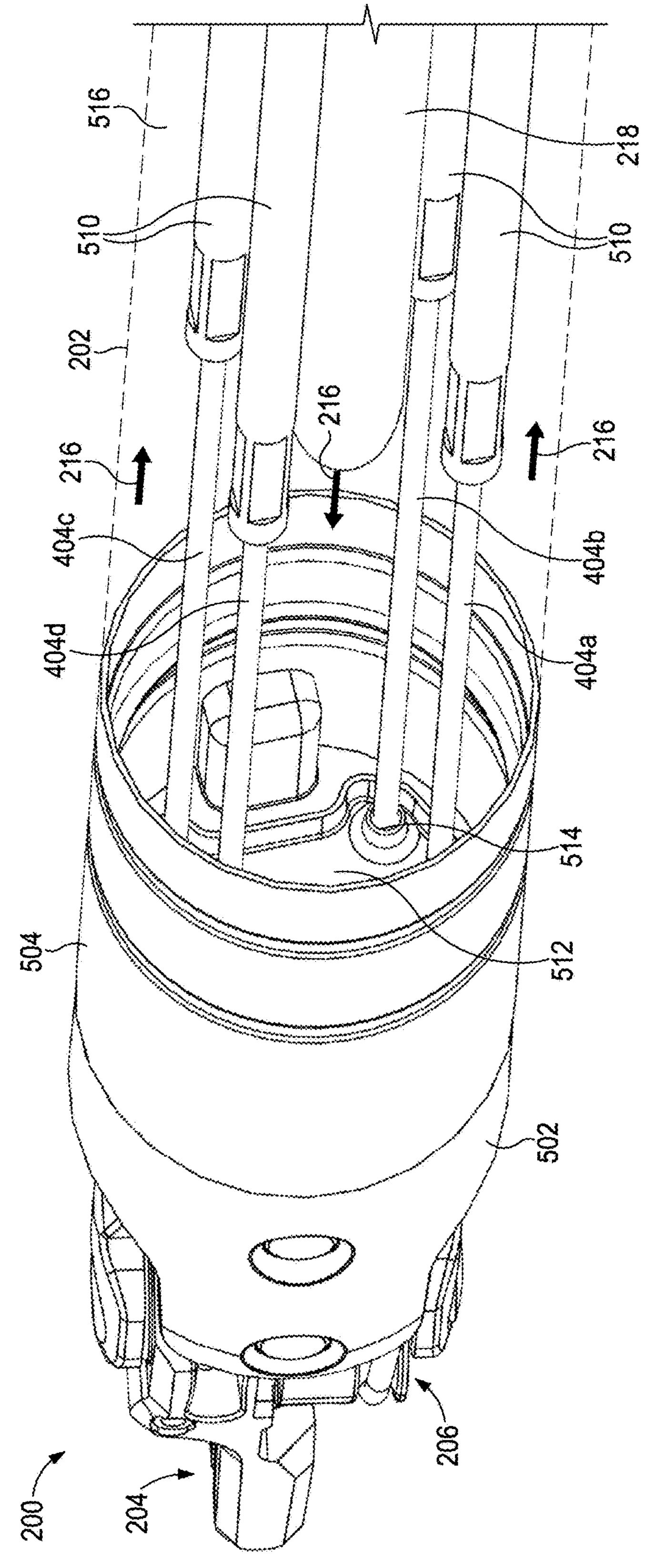

FIGS. 5A and 5B are cross-sectional and isometric views, respectively, of the distal end of the surgical tool 200, according to one or more embodiments of the present disclosure. More specifically, FIGS. 5A-5B depict the wrist 206 axially interposing the end effector 204 and the shaft 202. The distal end of the wrist 206 may be operatively coupled to the end effector 204, and the proximal end of the wrist 206 may be operatively coupled to the shaft 202. As illustrated, the wrist 206 may include a proximal clevis 502, and the shaft 202 may be operatively coupled to the wrist 206 at the proximal clevis 502. In some embodiments, the shaft 202 may be operatively coupled to the wrist 206 via a shaft adapter 504 that axially interposes the shaft 202 and the proximal clevis 502. In at least one embodiment, the shaft adapter 504 may comprise a sleeve that is roll crimped. In the illustrated embodiment, the shaft adapter 504 is mounted to the proximal clevis 502, and a distal end 506 (FIG. 5A) of the shaft 202 may be received within an interior of the shaft adapter 504. In other embodiments, however, the shaft 202 may be configured to be received about the exterior of the shaft adapter 504, without departing from the scope the disclosure. In yet other embodiments, the proximal clevis 502 is coupled to the shaft adaptor 504 by a rivet, and the shaft adaptor 504 is in turn coupled to the shaft 202 via crimping and a fastener. In other embodiments, the proximal clevis 502 can be directly coupled to the shaft 202 by a rivet.

As illustrated, the drive cables 404*a-d* extend from the shaft 202 and are redirected through the wrist 206 before terminating at the end effector 204. More specifically, one or more pulleys 508 (FIG. 5A) may be rotatably mounted to the proximal clevis 502 and configured to receive and reroute the drive cables 404*a-d* to the end effector 204. In at least one embodiment, as illustrated, each drive cable 404*a-d* may include or otherwise be crimped to an elongated hypotube 510 that extends longitudinally within the shaft 202. The hypotubes 510 may each be made of a rigid material (e.g., nylon, titanium, stainless steel, etc.) and may attach upper and lower portions of the drive cables 404*a-d*; e.g., portions of at or near the wrist 206 and portions within or near the drive housing 208 (FIG. 4).

The surgical tool 200 may further include a distal seal 512 arranged at the wrist 206. In the illustrated embodiment, the distal seal 512 is mounted to a portion of the proximal clevis 502, but could alternatively be mounted to (e.g., within) the shaft adapter 504. Alternatively, the distal seal 512 can be positioned between the proximal clevis 502 and the shaft 202 or the shaft adaptor 504. The distal seal 512 may be configured to provide a sealed interface or junction between the wrist 206 and the distal end 506 of the shaft 202. During surgical procedures, for example, the distal seal 512 helps prevent the migration of fluids, bioburden, and debris into the interior of the shaft 202 as the end effector 204 operates and the wrist 206 articulates.

The distal seal 512 may be made of a variety of semi rigid or flexible materials including, but not limited to, a rubber, nylon, a plastic, silicone, Teflon™, or any combination thereof. As illustrated, the distal seal 512 may provide or otherwise define a plurality of cable apertures 514, and each cable aperture 514 is configured to receive a corresponding one of the drive cables 404*a-d*. In some embodiments, the diameter of each aperture 514 may be slightly smaller than the diameter of the drive cables 404*a-d*, which helps provide a sealed interface between the distal seal 512 and the drive cables 404*a-d*. In the illustrated embodiment, the apertures 514 comprise protrusions extending proximally from the distal seal 512, but could alternatively be flush with the body of the distal seal 512.

The flush tube 218 extends within the shaft 202 and terminates prior to the wrist 206, and thus proximal to the distal seal 512. In an example flushing operation, the flushing fluid 216 circulates distally through the flush tube 218 and is eventually discharged from the flush tube 218 near the wrist 206 but proximal to the distal seal 512. Upon being discharged from the flush tube 218, the turbulent flow and pressure of the flushing fluid 216 operates to flush out debris and bioburden that may be present within the shaft 202 at or near the distal seal 512 and on the drive cables 404*a-d*. The flushing fluid 216, and any debris and bioburden entrained therein, may then circulate back up the shaft 202 in the proximal direction within an annulus 516 defined between the flush tube 218 and the inner diameter of the shaft 202. In some embodiments, the amount or intensity of the turbulence impacting the distal seal 512 and adjacent structural components may be adjusted by adjusting the position (location) of the distal end of the flush tube 218. In particular, the distal end of the flush tube 218 could be positioned (terminate) at the distal seal 512 or axially offset therefrom in the proximal direction by varying distances. Alternatively, or in addition thereto, the intensity of the turbulence could also be adjusted by altering the size and/or shape of the distal tip of the flush tube 218.

Figure 6:
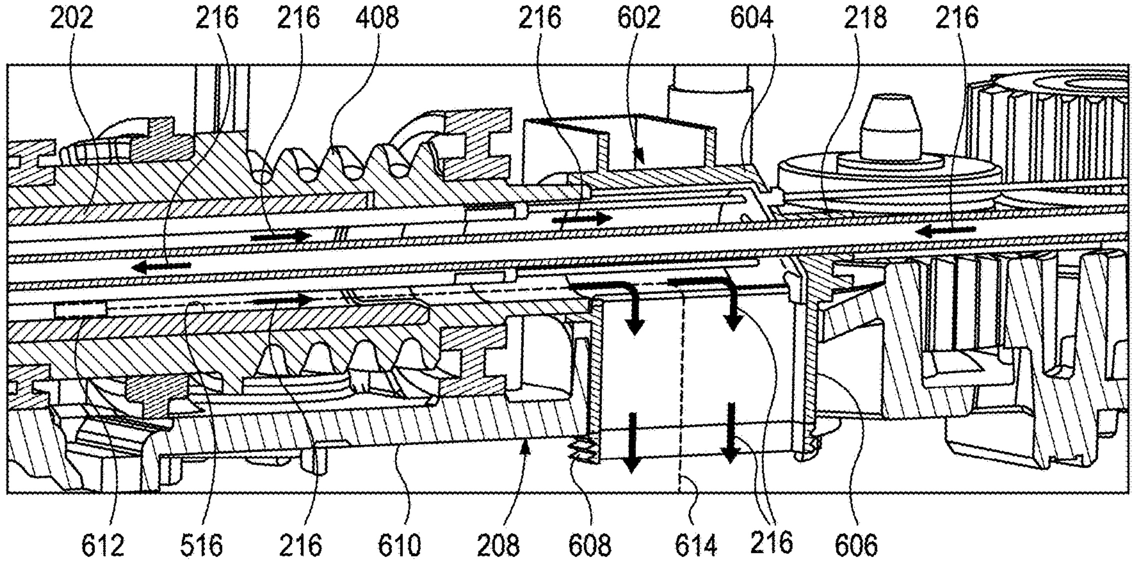
FIG. 6 is an enlarged, isometric cross-sectional side view of the interior of the drive housing of FIGS. 2 and 4, according to one or more embodiments.

FIG. 6 is an enlarged, isometric cross-sectional side view of the interior of the drive housing 208, according to one or more embodiments. As illustrated, the flush tube 218 extends within the shaft 202 and flushing fluid 216 is able to be circulated distally (i.e., to the left in FIG. 6) within the shaft 202. After being discharged from the distal end of the flush tube 218, as described above with reference to FIGS. 5A-5B, the flushing fluid 216 (along with any debris or bioburden entrained therein) is circulated back to the drive housing 208 within the annulus 516 defined between the flush tube 218 and the inner diameter the shaft 202.

As illustrated, the surgical tool 200 may further include a proximal drain 602 arranged within the drive housing 208 and in fluid communication with the annulus 516. In particular, the proximal drain 602 may be arranged to receive the flushing fluid 216 circulating back to the drive housing 208 from the distal end 506 (FIG. 5A) of the shaft 202. Upon encountering the proximal drain 602, the flushing fluid 216 may be discharged from (flow out of) the drive housing 208 via the proximal drain 602.

As illustrated, the proximal drain 602 includes an upper housing 604 and an outlet port 606 extending from and in fluid communication with the upper housing 604. The flushing fluid 216 reaching the proximal drain 602 is first received within the upper housing 604 and subsequently redirected into the outlet port 606 to be discharged (drained) from the drive housing 208. As illustrated, the flush tube 218 and the drive cables 404*a-d* (only cables 404*b* and 404*c* visible) extend through the proximal drain 602 and, more particularly, through the upper housing 604. Suitable apertures are provided and otherwise defined in the upper housing 604 to accommodate passage of the flush tube 218 and the drive cables 404*a-d*, as discussed below.

In some embodiments, the shaft 202 may be operatively coupled to the proximal drain 602 by extending into the interior of the upper housing 604, which would place the proximal drain 602 in fluid communication with the annulus 516. In other embodiments, however, the shaft 202 may be operatively coupled to the proximal drain 602 indirectly via the driven gear 408. More particularly, as illustrated, the driven gear 408 (e.g., a helical gear) is mounted to the shaft 202 and a proximal end of the driven gear 408 extends proximally to be received within the interior the upper housing 604. Accordingly, the proximal drain 602 may fluidly communicate with the annulus 516 via the driven gear 408, and the driven gear 408 may be able to rotate relative to the upper housing 604 during operation.

Figure 7A:
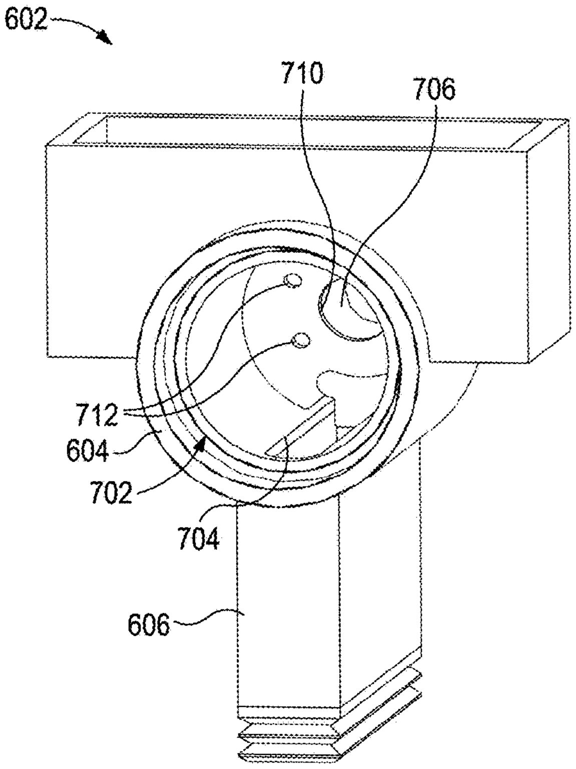
FIGS. 7A and 7B are isometric front and back views, respectively, of the proximal drain of FIG. 6, according to one or more embodiments.
Figure 7B:
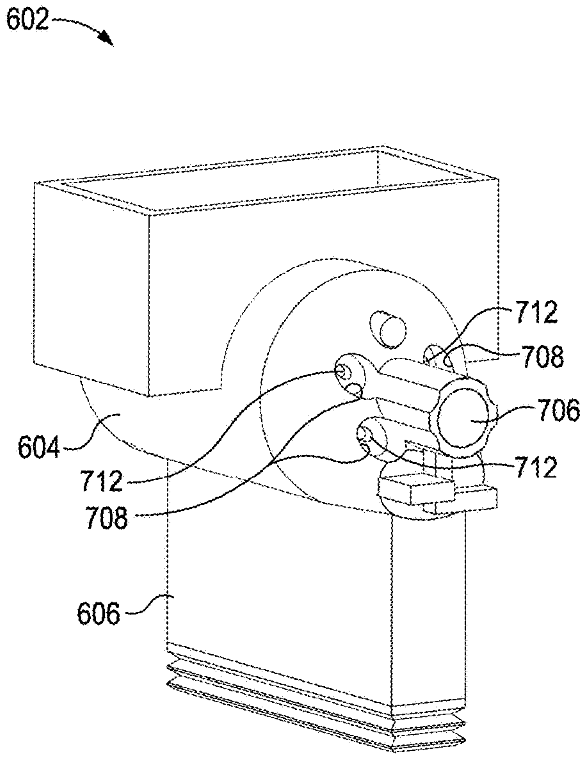

FIGS. 7A and 7B are isometric front and back views, respectively, of the proximal drain 602, according to one or more embodiments. As illustrated, the upper housing 604 may exhibit a generally circular cross-sectional shape, and the outlet port 606 may exhibit a generally rectangular cross-sectional shape. In other embodiments, however, the upper housing 604 may exhibit a polygonal cross-sectional shape, and the outlet port 606 may alternatively exhibit a circular cross-sectional shape, or any combination thereof, without departing from the scope of the disclosure. In some embodiments, the outlet port 606 extends substantially perpendicular from the upper housing 604, but could alternatively extend at an angle offset from perpendicular, without departing from the scope of the disclosure.

In some embodiments, as illustrated, the proximal drain 602 may include a drain sleeve 702 mounted (received) within the upper housing 604. The drain sleeve 702 may exhibit a cross-sectional shape that matches the cross-sectional shape of the interior of the upper housing 604. In the illustrated embodiment, for example, the drain sleeve 702 exhibits a generally circular cross-sectional shape, but could alternatively exhibit other cross-sectional shapes, depending on the cross-sectional shape of the upper housing 604.

In some embodiments, the drain sleeve 702 may be made of a flexible material, such as an elastomer or a rubber. In such embodiments, the drain sleeve 702 may be configured to sealingly engage the interior of the upper housing 604. The drain sleeve 702 may also provide or otherwise define a drain aperture 704 (FIG. 7A) configured to align with the outlet port 606, and thereby allow the flushing fluid 216 (FIG. 6) entering the proximal drain 602 to flow into the outlet port 606.

The upper housing 604 may define a housing central aperture 706 sized to receive the flush tube 218 (FIG. 6), and thereby allow the flush tube 218 to extend through the upper housing 604. The diameter of the housing central aperture 706 may be slightly larger than the diameter of the flush tube 218 to be able to accommodate the flush tube 218 during assembly. As best seen in FIG. 7B, the upper housing 604 may further define a plurality of housing cable apertures 708 sized to receive the drive cables 404*a-d* (FIGS. 4, 5A-5B, and 6). The housing cable apertures 708 may exhibit a diameter larger than the diameter of the drive cables 404*a-d*. Moreover, the housing cable apertures 708 may exhibit a diameter that is larger than a ball crimp (not shown) that may be secured to the end of the drive cables 404*a-d*. The enlarged diameter of the housing cable apertures 708 allows the ball crimp to pass therethrough during the assembly process of the surgical tool 200.

In embodiments where the drain sleeve 702 is received within the upper housing 604, the drain sleeve 702 may also define a sleeve central aperture 710 (FIG. 7A) configured to coaxially align with the housing central aperture 706. In some embodiments, the sleeve central aperture 710 may exhibit a diameter smaller than the diameter of the housing central aperture 706, which may prove advantageous in allowing the drain sleeve 702 to sealingly engage the outer circumference of the flush tube 208 when extended through the proximal drain 602.

The drain sleeve 702 may also include a plurality of sleeve cable apertures 712 configured to coaxially align with the housing cable apertures 708 defined in the upper housing 604 when the drain sleeve 702 is received within the upper housing 604. The sleeve cable apertures 712 defined in the drain sleeve 702 may exhibit a diameter smaller than the diameter of the housing cable apertures 708 of the upper housing 604. In at least one embodiment, for example, the diameter of the sleeve cable apertures 712 may be smaller than the diameter of the drive cables 404*a-d* (FIGS. 4, 5A-5B, and 6). In such embodiments, the drain sleeve 702 may sealingly engage the outer circumference of each drive cable 404*a-d*. Moreover, since the drain sleeve 702 is made of an elastomeric material, the diameter of the sleeve cable apertures 712 can elastically increase during assembly when it may be necessary to pass ball crimps secured to the drive cables 404*a-d* through the corresponding sleeve cable aperture 712. This feature may prove advantageous in allowing the drain sleeve 702 to be assembled onto the shaft subassembly after crimping the hypotubes 510 (FIGS. 5A-5B) onto the drive cables 404*a-d*.

Referring again to FIG. 6, in some embodiments, as illustrated, the proximal drain 602 may further include a skirt 608 attached to and extending from the end of the outlet port 606. The skirt 608 may be arranged and otherwise configured to extend past a bottom 610 of the drive housing 208. In some embodiments, for example, the outlet port 606 may extend to and terminate flush with the bottom 610, and the skirt 608 may extend past the bottom 610.

The skirt 608 may be made of a semi rigid or elastomeric material that makes the skirt 608 compliant such that when the drive housing 208 is mounted to a tool driver of a robotic manipulator, the skirt 608 will elastically conform to the opposing surface. In at least one embodiment, as illustrated, the skirt 608 may exhibit the general shape of an accordion, but other shapes may equally be employed, without departing from the scope of the disclosure.

The skirt 608 may prove advantageous in helping to form a sealed engagement with a tool driver of a robotic manipulator when the drive housing 208 is removably attached thereto. This may help in mitigating or preventing fluid ingress at the proximal end of the surgical tool 200, such as through a sterile adapter or during a procedure. Accordingly, the skirt 608 may help prevent fluids from migrating into the motors included in the tool driver.

In some embodiments, the drain sleeve 702 may facilitate the introduction of one or more tools 612 (shown in dashed lines) into the shaft (e.g., the annulus 516). The tool 612 may be secured to the end of a flexible conveyance 614 (also shown in dashed lines), such as a rod or wire made of a variety of materials including, but not limited to, a metal, nylon, a plastic, an elastomer, or any combination thereof. The tool 612 may comprise any tool or device that a user may desire to advance to the distal end 506 (FIG. 5A) of the shaft 202. In one or more embodiments, for example, the tool 612 may comprise a scope or camera used to visually verify if the flushing process successfully removed debris and bioburden present near the distal seal 512 (FIGS. 5A-5B) or along any part of the shaft 202. In such embodiments, the flexible conveyance 614 may comprise (or include) a transmission line used to communicate with a computer or the like. In other embodiments, the tool 612 may comprise a flexible cleaning brush that can be inserted into the shaft 202 (e.g., the annulus 516) to help remove soil, debris, and bioburden that may remain after the flushing process is complete (or during the flushing process).

Figure 8:
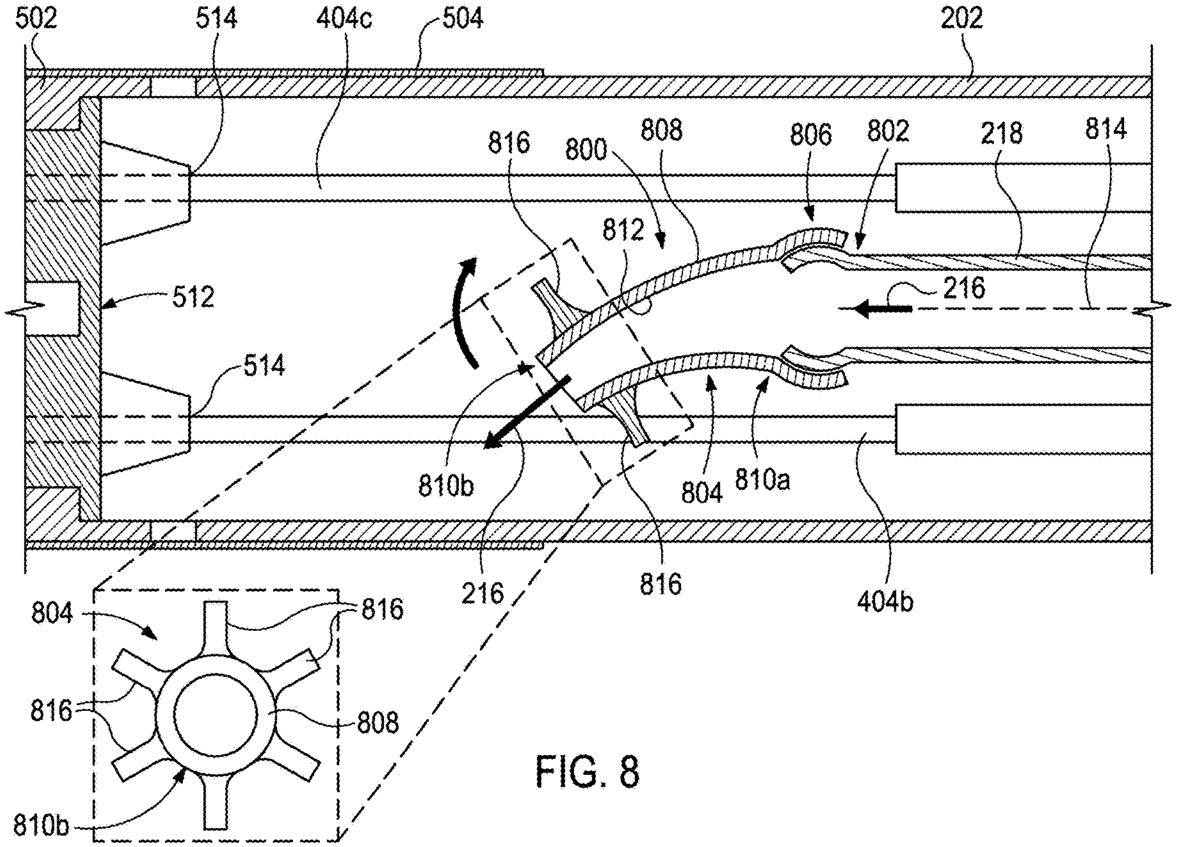
FIG. 8 is an enlarged cross-sectional side view of an example flush tube assembly, according to one or more embodiments of the present disclosure.

FIG. 8 is an enlarged cross-sectional side view of an example flush tube assembly 800, according to one or more embodiments of the present disclosure. More specifically, FIG. 8 depicts the distal seal 512 mounted to the proximal clevis 502, and the shaft 202 operatively coupled to the proximal clevis 502 via the shaft adapter 504. Moreover, the drive cables 404*a-d* (only cables 404*b* and 404*c* are shown) extend through the distal seal 512 at corresponding apertures 514.

The flush tube assembly 800 may be included at a distal end 802 of the flush tube 218 or may otherwise form an integral part of the flush tube 218. In the illustrated embodiment, the flush tube assembly 800 includes a nozzle 804 rotatably coupled to the distal end 802 of the flush tube 218 at a rotatable interface 806. The rotatable interface 806 may comprise any device or mechanism that allows the nozzle 804 to rotate relative to the flush tube 218; e.g., while the flush tube 218 remains stationary. In some embodiments, as illustrated, the rotatable interface 806 may comprise matable arcuate or bulbous features provided on the distal end 802 of the flush tube 218 and a proximal end of the nozzle 804. In such embodiments, to reduce friction, the arcuate features may be polished or a lubricant may be included at the interface between the arcuate features. In other embodiments, the rotatable interface 806 may include, but is not limited to, a ball bearing assembly, a ball joint, a cylindrical journal, an elastomeric joint, a living hinge, a lubricated gasket, or any combination thereof.

The nozzle 804 includes a body 808 that includes a first or "proximal" end 810*a* and a second or "distal" end 810*b* opposite the proximal end 810*a*. The proximal end 810*a* may be rotatably coupled to the distal end 802 of the flush tube 218, and the distal end 810*b* may provide a location where the flushing fluid 216 is discharged from the nozzle 804. The body 808 may define an inner flowpath 812 that extends between the proximal and distal ends 810*a,b*. In some embodiments, as illustrated, the diameter of the inner flowpath 812 may be smaller at the distal end 810*b* as compared the diameter at the proximal end 810*a*. The decreased diameter may increase the pressure within nozzle 804 such that the flushing fluid 216 is discharged from the nozzle 804 at increased pressures and velocities. This may prove advantageous in creating turbulence and cavitation to help remove debris and bioburden that may be present at or near the distal seal 512, on the inner surfaces of the shaft 202, and on the drive cables 404*a-d*.

In at least one embodiment, the diameter of the inner flow path 812 may progressively decrease between the proximal and distal ends 810*a,b*. In other embodiments, however, the diameter may alternatively decrease across only a portion of the inner flowpath 812, without departing from the scope of the disclosure.

In some embodiments, the body 808 may be curved or otherwise be angled away from a longitudinal axis 814 of the flush tube 218. Consequently, the flushing fluid 216 discharged from the nozzle 804 will be discharged toward an inner wall of the shaft 202 and not along the longitudinal axis 814. Moreover, the fluid pressure created within the nozzle 804 at or near the distal end 810*b* may place a lateral load on the nozzle 804, which may cause the nozzle 804 to rotate relative to the flush tube 218. In example operation, as the flushing fluid 216 is ejected from the nozzle 804, the fluid pressure will impel the nozzle 804 to rotate relative to the flush tube 218, which causes the flushing fluid 216 to be ejected in a swirl pattern (e.g., helix) such that all angular positions about the interior of the shaft 202 are impinged by the flushing fluid 216. As will be appreciated, this may help create turbulence at or near the distal seal 512 and agitate debris and bioburden for better cleaning.

In some embodiments, as illustrated, one or more radial projections 816 may extend radially outward from the body 808 at or near the distal end 810*b* of the nozzle 804. The radial projections 816 may operate as brushes or bristles configured to engage and "scrub" portions of the interior of the shaft 202, including portions of the drive cables 404*a-d*, as the nozzle 804 rotates during operation. As depicted in the enlarged inset graphic in FIG. 8, a plurality radial projections 816 may extend from the body 808. In some embodiments, as illustrated, the radial projections 816 may be equidistantly spaced from each other about the outer circumference of the body 808, but could alternatively be non-equidistantly spaced. The radial projections 816 may be made of a flexible or pliable material, such as silicone or the like. The flexible material of the radial projections 816 ensures that engaging the drive cables 404*a-d* (or any other structure within the shaft 202) during operation will not result in damage.

Figure 9:
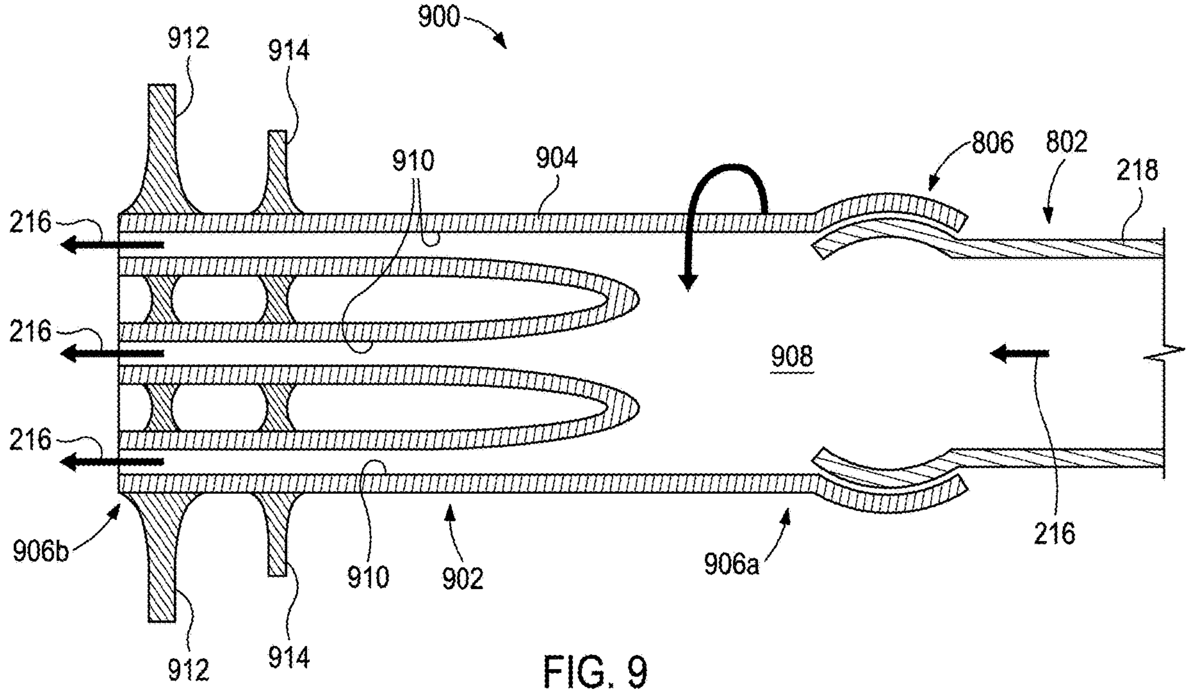
FIG. 9 is an enlarged cross-sectional side view of another example flush tube assembly, according to one or more additional embodiments of the present disclosure.

FIG. 9 is an enlarged cross-sectional side view of another example flush tube assembly 900, according to one or more additional embodiments of the present disclosure. The flush tube assembly 900 may be similar in some respects to the flush tube assembly 800 of FIG. 8, and therefore may be best understood with reference thereto. In some applications, the flush tube assembly 900 may replace the flush tube assembly 800 of FIG. 8, and may thus be used to help remove debris and bioburden near the distal seal 512 (FIG. 8) and within the shaft 202 (FIG. 2). As illustrated, the flush tube assembly 900 may be included at the distal end 802 of the flush tube 218 or may otherwise form an integral part of the flush tube 218. Moreover, the flush tube assembly 900 includes a nozzle 902 rotatably coupled to the distal end 802 of the flush tube 218 at the rotatable interface 806.

The nozzle 902 includes a body 904 that includes a first or "proximal" end 906*a* and a second or "distal" end 906*b* opposite the proximal end 906*a*. The proximal end 906*a* may be rotatably coupled to the flush tube 218 at the rotatable interface 806, and the distal end 906*b* is where the flushing fluid 216 is discharged from the nozzle 902. The body 904 defines an inner flowpath 908 that extends between the proximal and distal ends 906*a,b*. In some embodiments, as illustrated, the inner flowpath 908 may divide (separate) into two or more flow channels 910 (three shown), thus characterizing the nozzle 902 as a type of multi-tube nozzle. The diameter of the flow channels 910 are smaller than the diameter of the inner flowpath 908. In some embodiments, the diameter of each flow channel 910 may be the same, but could alternatively be different. Moreover, in some embodiments, the flow channels 910 may extend substantially parallel to each other, but could alternatively extend at an angle relative to each other, without departing from the scope of the disclosure.

The smaller diameter flow channels 910 may cause the pressure within the nozzle 902 to increase such that the flushing fluid 216 is discharged from the nozzle 902 at increased pressures and velocities. This may prove advantageous in creating turbulence and cavitation to help remove debris and bioburden that may be present at or near the distal seal 512 (FIG. 8), on the inner surfaces of the shaft 202 (FIG. 8), and on the drive cables 404*a-d* (FIG. 8). In other embodiments, or in addition thereto, the spacing of the flow channels 910 may be designed such that an unbalanced flow results as the flushing fluid 216 is discharged from the nozzle 902. This may prove advantageous in making it less likely that the discharged flow reaches a laminar steady state, but instead helps to maintain a more turbulent flow over time, which helps remove the debris and bioburden. Moreover, the fluid pressure created within the nozzle 902 at or near the distal end 906*b* may cause the nozzle 902 to rotate relative to the flush tube 218. As will be appreciated, this may also help create turbulence near the distal seal 512 to help agitate the debris and bioburden present at or near the distal seal 512.

In some embodiments, as illustrated, one or more radial projections 912 may extend radially outward from the body 904 at or near the distal end 906*b* of the nozzle 902. The radial projections 912 may operate as brushes or bristles configured to engage and "scrub" portions of the interior of the shaft 202, including portions of the drive cables 404*a-d*. The radial projections 912 may be equidistantly or non-equidistantly spaced from each other about the outer circumference of the body 904. Moreover, the radial projections 912 may be made of a flexible or pliable material, such as silicone, an elastomer, a soft material (e.g., nylon, polytetrafluoroethylene or "PTFE"), or the like, such that engaging structures within the shaft 202 (FIG. 8) during operation will not cause damage.

In one or more embodiments, the nozzle 902 may further include one or more backup or "secondary" radial projections 914 extending radially outward from the body at or near the distal end 906*b* of the nozzle 902, but axially offset from (e.g., located proximal to) the radial projections 912. In embodiments that include the secondary radial projections 914, the radial projections 912 may be characterized and otherwise referred to as "primary" radial projections 912. Similar to the primary radial projections 912, the secondary radial projections 914 may be equidistantly or non-equidistantly spaced from each other about the outer body 904. Moreover, the secondary radial projections may be made of flexible or pliable materials that will not damage structures as the nozzle 902 rotates.

Unlike the primary radial projections 912, however, the secondary radial projections 914 may be smaller than the primary radial projections 912. In the illustrated embodiment, for example, the height or distance that the secondary radial projections 914 extend from the outer circumference of the body 904 is smaller than the height or distance that the primary radial projections 912 extend from the outer circumference. In other embodiments, however, secondary radial projections 914 may exhibit a larger height as compared to the primary radial projections 512, without departing from the scope of the disclosure.

Figure 10A:
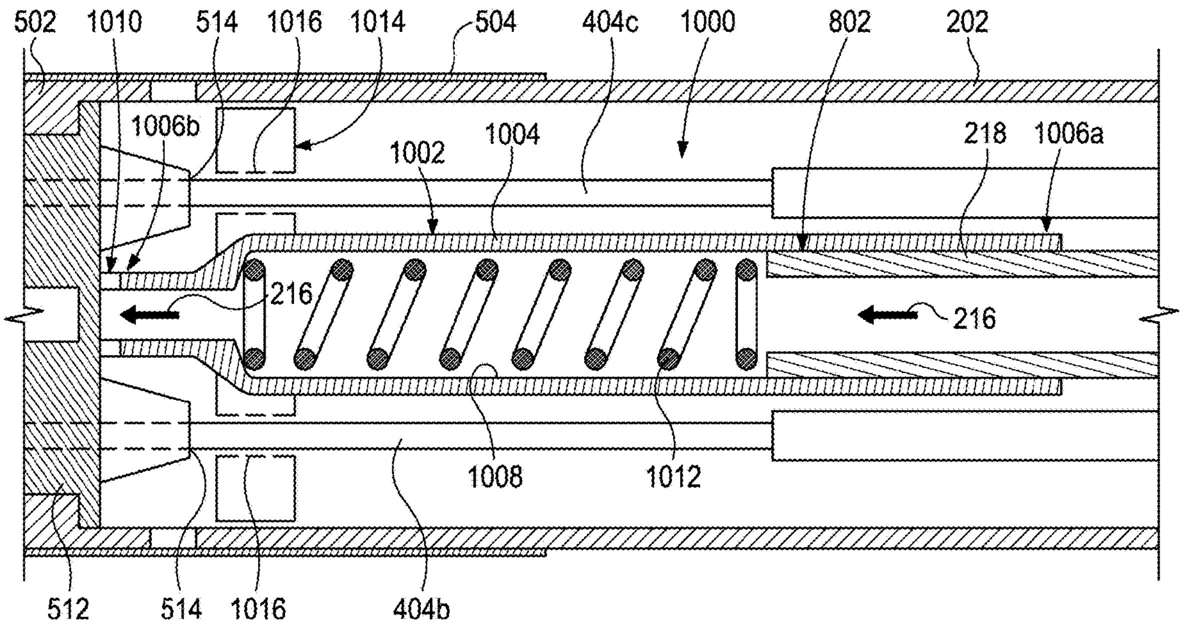
FIG. 10A is an enlarged cross-sectional side view of another example flush tube assembly, according to one or more additional embodiments of the present disclosure.

FIG. 10A is an enlarged cross-sectional side view of another example flush tube assembly 1000, according to one or more additional embodiments of the present disclosure. FIG. 10A depicts the distal seal 512 mounted to the proximal clevis 502, and the shaft 202 is operatively coupled to the proximal clevis 502 via the shaft adapter 504. Moreover, the drive cables 404*a-d* (only cables 404*b* and 404*c* are shown) extend through the distal seal 512 at corresponding apertures 514.

The flush tube assembly 1000 may be included at the distal end 802 of the flush tube 218 or may otherwise form an integral part of the flush tube 218. In the illustrated embodiment, the flush tube assembly 1000 includes a nozzle 1002 mounted to the flush tube 218 and able to move axially relative to the flush tube 218. The nozzle 1002 includes a body 1004 that includes a first or "proximal" end 1006*a* and a second or "distal" end 1006*b* opposite the proximal end 1006*a*. The proximal end 1006*a* may be slidably (movably) mounted to the distal end 802 of the flush tube 218, and the distal end 1006*b* may provide a location where the flushing fluid 216 is discharged from the nozzle 1002.

The body 1004 defines an inner flowpath 1008 that extends between the proximal and distal ends 1006*a,b*. In some embodiments, as illustrated, the diameter of the inner flowpath 1008 may be smaller at the distal end 1006*b* as compared the diameter at the proximal end 1006*a*, which may cause the flushing fluid 216 to be discharged from the nozzle 1002 at increased pressures and velocities. This may prove advantageous in creating turbulence and cavitation to help remove debris and bioburden that may be present at or near the distal seal 512, on the inner surfaces of the shaft 202, and on the drive cables 404*a-d*. In some embodiments, as illustrated, the tip of the nozzle 1002 at the distal end 1006*b* may include one or more apertures or castellations 1010 that help facilitate fluid flow out of the nozzle 1002 in various angular orientations (directions).

In some embodiments, the flush tube assembly 1000 may be arranged such that the nozzle 1002 naturally engages the distal seal 512. The nozzle 1002, however, may be movable between a first or "extended" position and a second or "retracted" position. The nozzle 1002 is shown in FIG. 10A in the extended position, where the distal tip of the nozzle 1002 engages (or comes into close contact with) distal seal 512. The nozzle 1002 can be moved (transitioned) to the retracted position by circulating the flushing fluid 216 through the flush tube 218 and into the inner flowpath 1008. Because of the reduced diameter of the inner flowpath 1008 at or near the distal end 1006*b* of the nozzle 1002, the pressure within the body 1004 increases and the flushing fluid 216 is ejected from the nozzle 1002 at a high velocity, which causes the nozzle 1002 translate proximally.

In some embodiments, as illustrated, a spring 1012 may be arranged within the inner flowpath 1008 and configured to naturally bias the nozzle 1002 to the extended position. As the nozzle 1002 is urged in the proximal direction during operation, the spring 1012 compresses and builds spring force. Once flow of the flushing fluid 216 through the nozzle 1002 ceases, however, the pressure within the inner flowpath 1008 correspondingly decreases and thereby allows the spring force to release and transition the nozzle 1002 back to the extended position.

In some embodiments, as illustrated, a radial projection 1014 may extend radially outward from the body 1004 at or near the distal end 1006*b* of the nozzle 1002. The radial projection 1014 may operate to engage and "scrub" portions of the interior of the shaft 202 as the nozzle 1002 transitions between the extended and retracted positions. In one or more embodiments, cable apertures 1016 may be defined in the radial projection 1014 to accommodate the drive cables 404*a-d*. As the nozzle 1002 transitions between the extended and retracted positions, the drive cables 404*a-d* are fed through the corresponding cable apertures 1016, which may prove advantageous in cleaning the drive cables 404*a-d* from debris and bioburden.

Figure 10B:
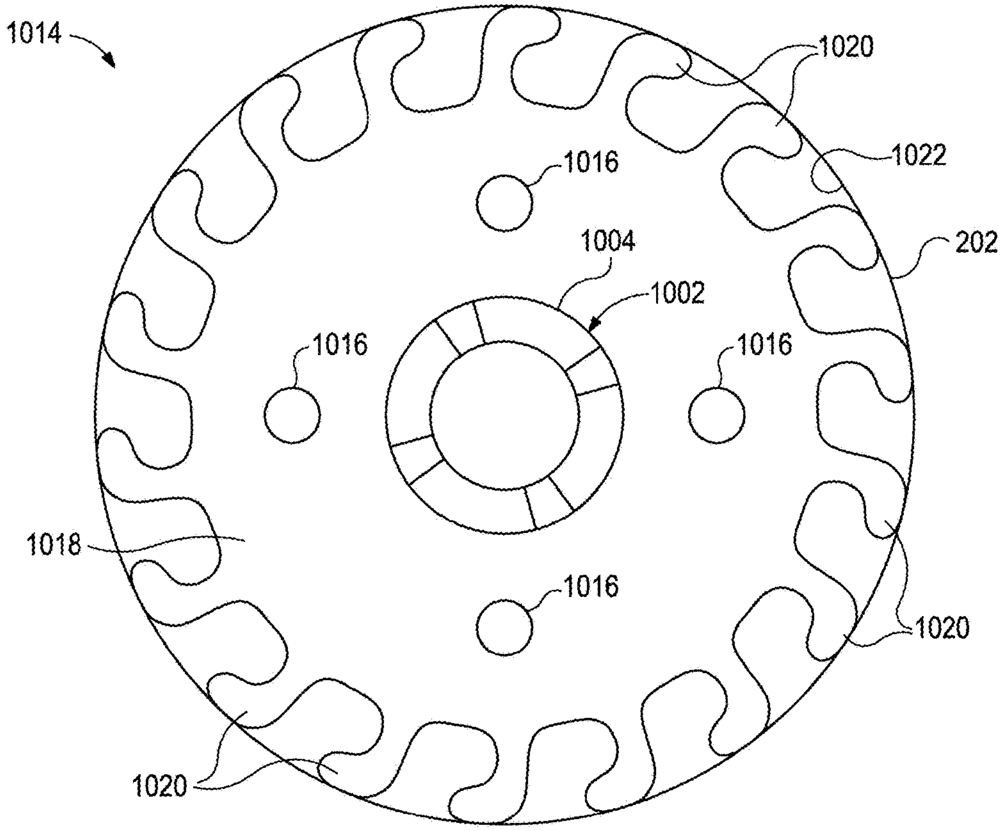
FIG. 10B is a schematic end view of an example of the radial projections of FIG. 10A, according to one or more embodiments of the disclosure.

Referring to FIG. 10B, with continued reference to FIG. 10A, illustrated is a schematic end view of an example of the radial projection 1014, according to one or more embodiments of the disclosure. As illustrated, the radial projection 1014 includes a generally circular body 1018 that is mounted to the body 1004 of the nozzle 1002. Moreover, the cable apertures 1016 may be defined in the body 1018 to accommodate the drive cables 404*a-d* (FIG. 10A), as described above.

As illustrated, the radial projection 1014 can include a plurality of radially-extending fingers 1020 that extend from the body 1018 to engage or come into close contact with an inner surface 1022 of the shaft 202. In some embodiments, as illustrated, the fingers 1020 may be equidistantly spaced from each other about the outer circumference of the body 1018, but could alternatively be non-equidistantly spaced. Moreover, the fingers 1020 may be made of a flexible or pliable material, such as silicone, an elastomer, a soft material (e.g., nylon, polytetrafluoroethylene or "PTFE"), or the like. This may prove advantageous in allowing the fingers 1020 to engage and clean the inner surface 1022 of the shaft 202 as the nozzle 1000 transitions between the extended and retracted positions during operation.

Figure 11A:
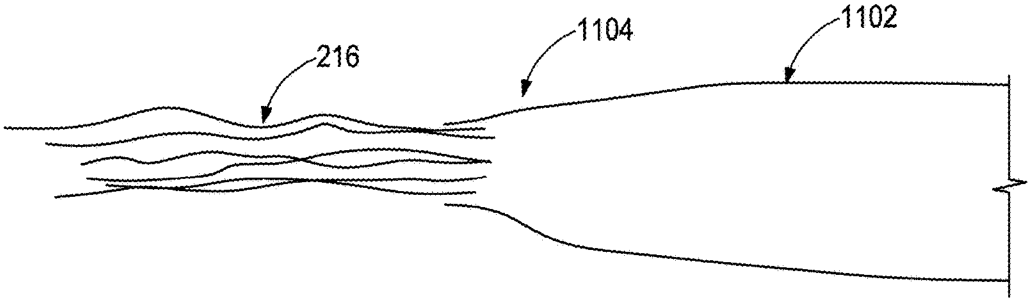
FIGS. 11A-11C are alternative example flush tubes that may be used in accordance with the principles of the present disclosure.
Figure 11B:
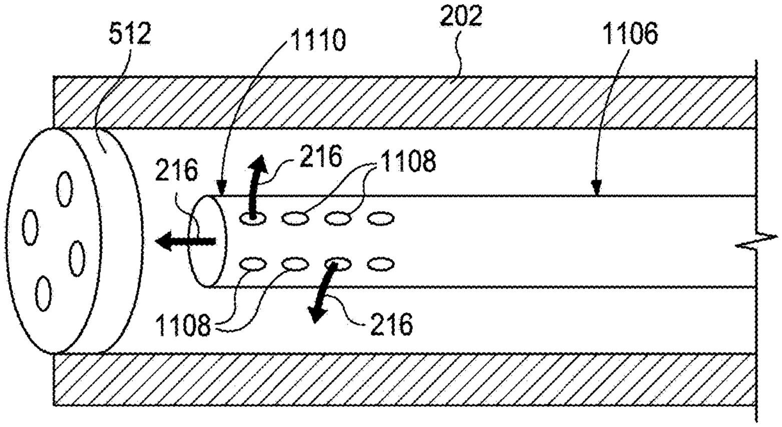
Figure 11C:
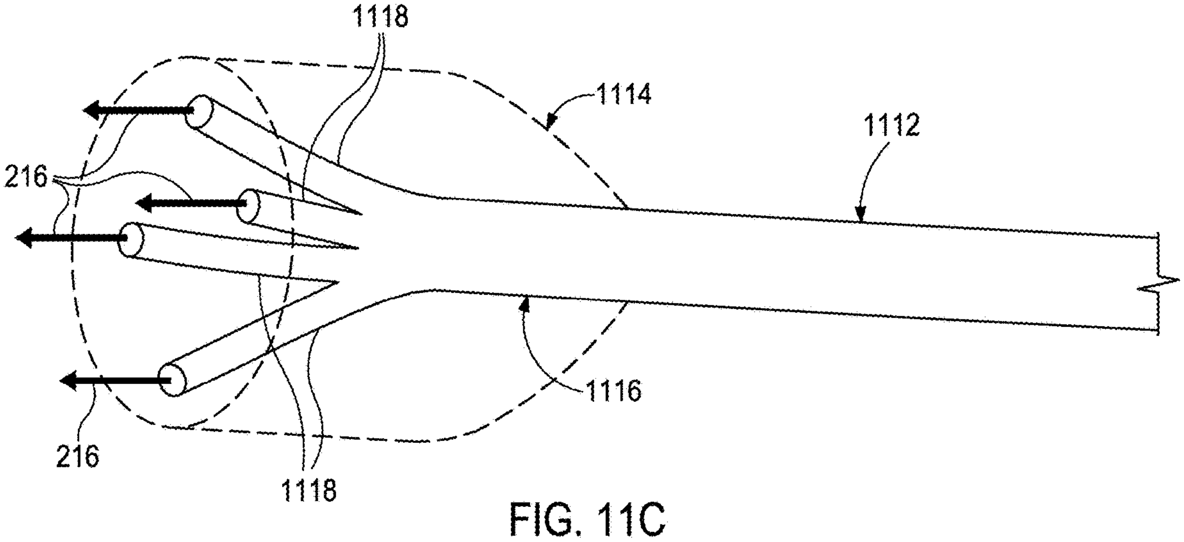

FIGS. 11A-11C are schematic diagrams of example flush tubes that may be used in accordance with the principles of the present disclosure. The flush tubes shown in FIGS. 11A-11C are similar in some respects to the flush tube 218 of FIGS. 2, 4, and 5A-5B, and therefore may be best understood with reference thereto. Similar to the flush tube 218, for example, each flush tube shown in FIGS. 11A-11C may be configured to convey the flushing fluid 216 from the drive housing 208 (FIGS. 2, 4, 5A-5B) to at or near the wrist 206 (FIGS. 2, 4, 5A-5B) to help flush out debris and bioburden that may be present within the shaft 202 (FIGS. 2, 4, 5A-5B).

FIG. 11A depicts a flush tube 1102 having a distal end 1104 that tapers and otherwise exhibits a reduced diameter as compared to remaining portions of the flush tube 1102. The reduced diameter distal end 1104 may effectively act as a nozzle that increases the pressure of the flushing fluid 216, and ejects the flushing fluid 216 at an increased velocity. In at least one embodiment, the flushing fluid 216 may be ejected from the flush tube 1102 in a substantially laminar flow.

Conventional flush tubes typically have a square face and crimp geometry, which has the potential for catching on shoulders or other obstructions as the flush tube is extended within the shaft during assembly. The flush tube 1102 of FIG. 11A, however, includes the tapered distal end 1104, which eliminates this issue. In at least one embodiment, the interior of the flush tube 1102 may be electro-polished.

FIG. 11B depicts a flush tube 1106 with a plurality of holes or nozzles 1108 defined at or near a distal end 1110 of the flush tube 1106. In some embodiments, the nozzles 1108 may be drilled equidistantly about the outer circumference of the flush tube 1106, but could alternatively be defined at predetermined angles configured to direct high-pressure flow at difficult to clean the areas on the proximal side of the distal seal 512. The resultant flow out of the nozzles 1108 may help to activate the proximal flow, and could make the discharge more turbulent to improve cleaning. Moreover, in some embodiments, the nozzles 1108 may be provided not just near the distal end 1110 of the flush tube 1106, but along all or a majority of the axial length of the flush tube 1106.

FIG. 11C depicts a flush tube 1112 that includes a nozzle 1114 (shown in dashed lines) attached to or forming part of a distal end 1116 of the flush tube 1112. As illustrated, the nozzle 1114 may define a plurality of spray conduits 1118 extending distally and radially away from the flush tube 1112. The spray conduits 1118 may receive the flushing fluid 216 from the flush tube 1112, and convey the flushing fluid 216 toward difficult to reach areas at or near the distal seal 512 (FIG. 11B) and with varying amounts of pressure based on the diameter of the spray conduit 1118. In the illustrated embodiment, four spray conduits 1118 are depicted, but the nozzle 1114 can include more or less than four spray conduits 1118, without departing from the scope of the present disclosure.

Figure 12A:
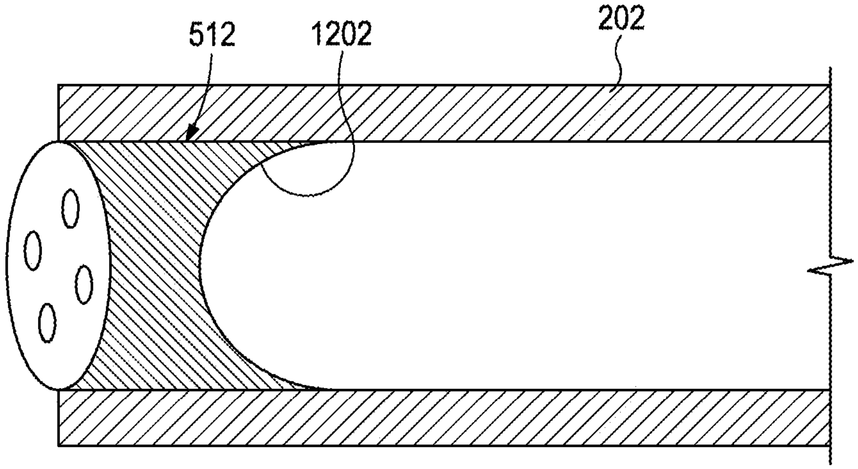
FIGS. 12A and 12B depict alternative embodiments of the shaft and the distal seal, according to one or more additional embodiments.
Figure 12B:
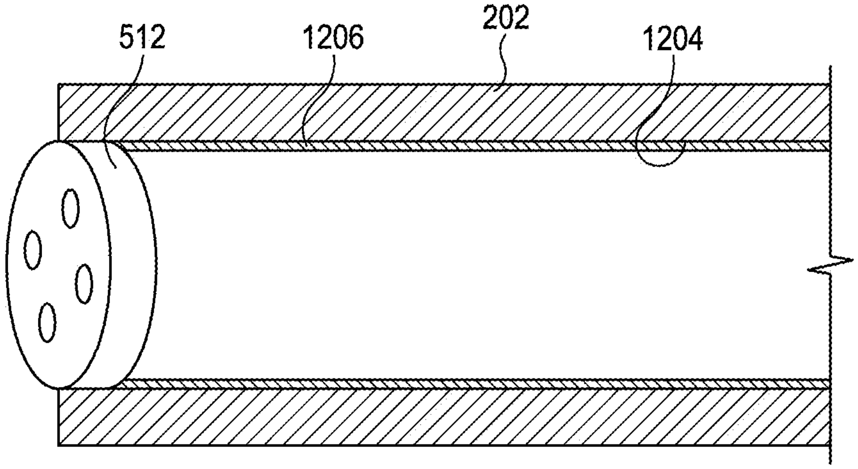

FIGS. 12A and 12B depict alternative embodiments of the shaft 202 and the distal seal 512, according to one or more additional embodiments. In FIG. 12A, the proximal end of the distal seal 512 (i.e., the end exposed to the interior of the shaft 202) exhibits a generally concave shape otherwise includes or defines a fillet 1202. The fillet 1202 may extend about the entire outer periphery of the distal seal 512 at or near the inner wall of the shaft 202. The concave nature of the fillet 1202 may prove advantageous in reducing the surface tension of any fluids, debris, and bioburden that may collect in corners at the distal seal 512.

In FIG. 12B, the inner diameter or inner wall 1204 of the shaft 202 may be coated with a hydrophobic material 1206. In some embodiments, portions of the distal seal 512 exposed to the interior of the shaft 202 may also be coated with the hydrophobic material 1206. The hydrophobic material 1206 may ease the cleaning process since fluids, debris, and bioburden will have less propensity of sticking to surfaces coated with the hydrophobic material 1206.

Figure 13:
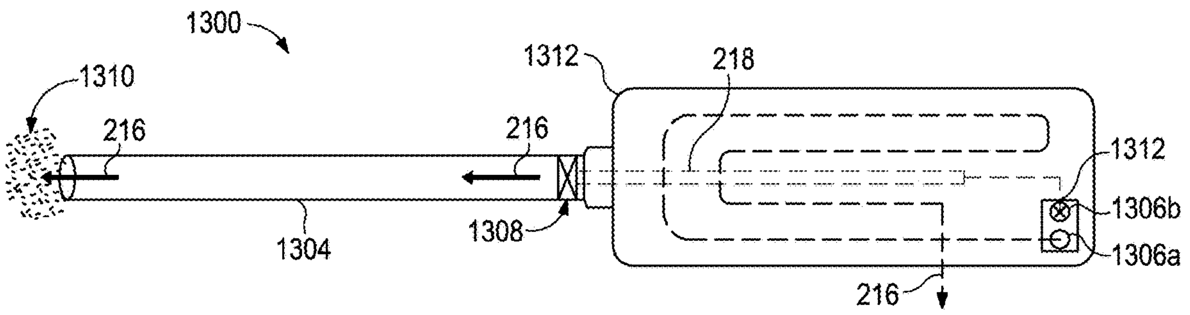
FIG. 13 is a schematic side view of another example surgical tool may incorporate the principles of the present disclosure.

FIG. 13 is a schematic side view of an example surgical tool 1300 that may incorporate the principles of the present disclosure. As illustrated, the surgical tool includes a drive housing 1302 and a shaft 1304 extending distally from the drive housing. The drive housing 1302 may be the same as or similar to the drive housing 208 of FIG. 2. As illustrated, first and second flush ports 1306*a* and 1306*b* may be provided on the drive housing 1302 to provide a means to introduce the flushing fluid 216 into the surgical tool 200 during cleaning and sterilization.

The flushing fluid 216 is introduced into the drive housing 1302 via the first flush port 1306*a*. In such applications, the flushing fluid 216 is then circulated throughout the interior of the drive housing 1302 before being discharged from the drive housing 1302 via various apertures, drains, holes, etc. defined in the drive housing 1302. Any debris or bioburden that may be present within the drive housing 1302 may be entrained within the flushing fluid 216 and flushed out of the drive housing 1302.

In contrast, the flushing fluid 216 provided to the second flush port 1306*b* may fluidly communicate with the flush tube 218 (shown in dashed lines), which extends longitudinally within the drive housing 1302. In prior embodiments discussed herein, the flush tube 218 would extend distally within the shaft 1304 and discharge the flushing fluid 216 at or near the distal seal 512 (FIGS. 5A-5B) to remove debris and bioburden accumulating at the distal seal 512 and within the shaft. In the present embodiment, however, the distal seal 512 is omitted, and the surgical tool 1300 may instead include a proximal seal 1308 arranged at or near the proximal end of the shaft 1304. The flush tube 218 extends to and terminates at the proximal seal 1308, thereby discharging the flushing fluid 216 into the interior of the shaft 1304 at or near the proximal end of the shaft 1304. The flushing fluid 216 then circulates to the distal end of the shaft 1304 and is discharged from the shaft 1304 along with debris and bioburden 1310 that may have accumulated within the shaft 1304 during operation of the surgical tool 1300. Accordingly, the proximal seal 1308 enables a user to easily clean the surgical tool 1300 by flushing the debris and bioburden 1310 down and out the distal end of the shaft 1304, rather than potentially back into the drive housing 1302.

Figure 14:
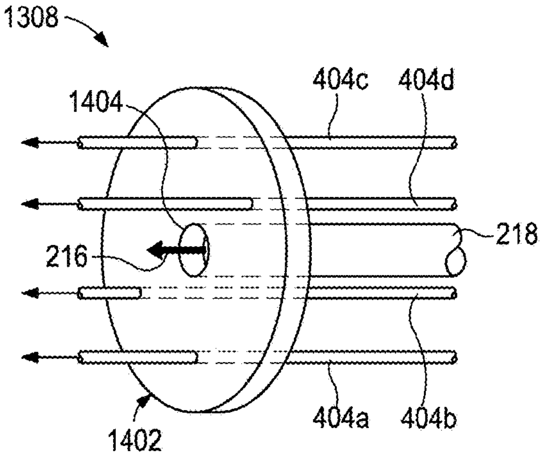
FIG. 14 is an isometric, schematic view of an example of the proximal seal of FIG. 13, according to one or more embodiments.

FIG. 14 is an isometric, schematic view of an example of the proximal seal 1308, according to one or more embodiments. As illustrated, the proximal seal 1308 provides a generally circular or disc-shaped body 1402. The diameter of the body 1402 may be sized such that a sealed engagement is created against the inner surface of the shaft 1304 (FIG. 13). The sealed engagement provided by the proximal seal 1308 helps to ensure that insufflation is maintained during operation of the surgical tool 1300 (FIG. 13).

The body 1402 also defines a central aperture 1404 configured to receive and sealingly engage the outer circumference of the flush tube 218. As illustrated, the flush tube 218 terminates at the proximal seal 1308. Accordingly, the flushing fluid 216 conveyed within the flush tube 218 is discharged from the flush tube 218 at the proximal seal 1308. In some embodiments, as illustrated, the central aperture 1404 may be defined at the center of the body 1402, but could alternatively be defined offset from the center, without departing from the scope the disclosure. In some embodiments, the flush tube 218 may be sealingly engaged to the body 1402 at the central aperture 1404 using a lip seal, or the like. In such embodiments, the sealed engagement will provide a small amount of interference between the flush tube 218 and the seal, but simultaneously enable rotation of the shaft 1304 (FIG. 13) during operation of the surgical tool 1300 (FIG. 13).

While the proximal seal 1308 is shown in FIG. 14 exhibiting a generally circular and disc-shaped structure, it is contemplated herein that the geometry of the proximal seal 1308 may be altered to fit various applications. In one or more embodiments, for example, the proximal seal 1308 may be similar to the distal seal 512 shown in FIG. 12A, and may thus exhibit a generally concave shape that provides or defines a fillet to reduce the surface tension of any fluids, debris, and bioburden that may collect in corners at the proximal seal 1308. Moreover, in some embodiments, the distal end of the flush tube 218 may include or provide a nozzle or the like to help produce turbulent flow.

The body 1402 may also provide a plurality of cable apertures 1406 through which the drive cables 404*a-d* may extend. In some embodiments, the diameter of the cable apertures 1406 may be slightly less than the outer diameter of the drive cables 404*a-d*. In such embodiments, the proximal seal 1308 may be configured to sealingly engage the outer circumference of the drive cables 404*a-d*, which may also help maintain insufflation during operation.

Figure 15:
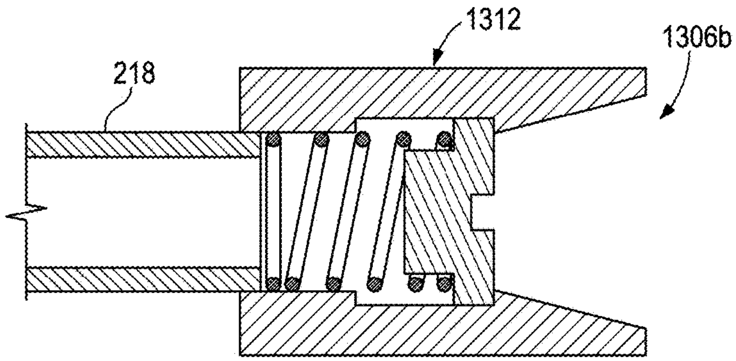
FIG. 15 is a cross-sectional side view of one example of the check valve of FIG. 14, according to one or more embodiments of the present disclosure.

Referring briefly again to FIG. 13, in some embodiments, the surgical tool 1300 may further include a check valve 1312 provided at the second flush port 1306*b*. FIG. 15 is a cross-sectional side view of one example of the check valve 1312, according to one or more embodiments of the present disclosure. As illustrated, the check valve 1312 may be spring-loaded and include a Luer fitting with an approximate 6° taper. Moreover, the flush tube 218 (or a conduit or plumbing extending to the flush tube 218) may be operatively coupled to the check valve 1312. In at least one embodiment, the flush tube 218 may be operatively coupled to the check valve 1312 using a barb fitting or the like.

Embodiments disclosed herein include:

A. A surgical tool includes a drive housing, a shaft extending distally from the drive housing, a distal seal arranged at a distal end of the shaft, a flush tube extending from the drive housing within the shaft and terminating proximal to the distal seal, wherein a flushing fluid conveyed distally through the flush tube is discharged from the flush tube and impinges upon the distal seal, and a proximal drain arranged within the drive housing and in fluid communication with an annulus defined between the flush tube and an inner wall of the shaft, wherein the flushing fluid discharged from the flush tube circulates proximally within the annulus to the proximal drain to be discharged from the drive housing.

B. A flush tube assembly includes a nozzle rotatably coupled to a distal end of a flush tube, the flush tube being extendable within a shaft extending from a drive housing of a surgical tool, and an inner flowpath extending between proximal and distal ends of the nozzle, wherein circulating a flushing fluid through the inner flowpath causes the nozzle to rotate relative to the flush tube.

C. A method of flushing a surgical tool includes conveying a flushing fluid into a flush tube arranged within a shaft extending distally from a drive housing of the surgical tool, discharging the flushing fluid from the flush tube proximal to a distal seal arranged at a distal end of the shaft, impinging the flushing fluid on the distal seal and portions of the shaft and thereby removing debris and bioburden from the distal seal, circulating the flushing fluid back to the drive housing within an annulus defined between the flush tube and an inner wall of the shaft, receiving the flushing fluid at a proximal drain arranged within the drive housing and in fluid communication with the annulus, and discharging the flushing fluid from the drive housing via the proximal drain.

Each of embodiments A, B, and C may have one or more of the following additional elements in any combination: Element 1: further comprising an end effector operatively coupled to the distal end of the shaft, and a wrist interposing the end effector and the distal end of the shaft, wherein the distal seal is mounted to the wrist. Element 2: wherein the proximal drain includes an upper housing in fluid communication with the annulus, and an outlet port extending from the upper housing. Element 3: wherein the shaft is operatively coupled to the upper housing within the drive housing. Element 4: wherein a driven gear is mounted to the shaft within the drive housing, and a proximal end of the driven gear extends into an interior of the upper housing and thereby operatively couples the shaft to the upper housing. Element 5: wherein the upper housing defines a housing central aperture sized to receive the flush tube extending through the upper housing, and a plurality of housing cable apertures sized to receive a corresponding plurality of drive cables extending from the drive housing and through the distal seal. Element 6: further comprising a drain sleeve received within the upper housing and providing a sleeve central aperture coaxially alignable with the housing central aperture to receive the flush tube, a plurality of sleeve cable apertures coaxially alignable with the plurality of housing cable apertures, and a drain aperture alignable with the outlet port to allow the flushing fluid entering the proximal drain to flow into the outlet port. Element 7: wherein each sleeve cable aperture exhibits a diameter smaller than a diameter of each housing cable aperture to sealingly engage an outer circumference of each drive cable. Element 8: wherein the proximal drain further includes a skirt extending from the outlet port and past a bottom of the drive housing.

Element 9: wherein the nozzle is curved away from a longitudinal axis of the flush tube. Element 10: further comprising one or more radial projections extending radially outward from the body at the distal end of the body. Element 11: wherein the inner flowpath separates into two or more flow channels exhibiting a diameter smaller than a diameter of the inner flowpath at the proximal end of the nozzle. Element 12: wherein the nozzle is movable between an extended position, where a distal end of the nozzle engages the distal seal, and a retracted position, where the nozzle moves proximally relative to the flush tube, and wherein a diameter of the inner flowpath at the distal end of the nozzle is smaller than a diameter at the proximal end of the nozzle thereby helping to transition the nozzle between the extended and retracted positions as flushing fluid is circulated through the inner flowpath. Element 13: wherein the flush tube assembly further includes a radial projection extending radially outward from the nozzle having a plurality of radially-extending fingers extending from the body to an inner surface of the shaft.

Element 14: wherein the proximal drain includes an upper housing in fluid communication with the annulus, and an outlet port extending from the upper housing, the upper housing defining a housing central aperture sized to receive the flush tube extending through the upper housing, and a plurality of housing cable apertures sized to receive a corresponding plurality of drive cables extending from the drive housing and through the distal seal, the method further comprising receiving the flushing fluid from the annulus at the upper housing, and discharging the flushing fluid from the proximal drain at the outlet port. Element 15: wherein a drain sleeve is received within the upper housing and provides a sleeve central aperture coaxially alignable with the housing central aperture to receive the flush tube, and a plurality of sleeve cable apertures coaxially alignable with the plurality of housing cable apertures, the method further comprising sealingly engaging an outer surface of the flush tube with the sleeve central aperture, and sealingly engaging an outer surface of each drive cable with the plurality of sleeve cable apertures. Element 16: wherein a skirt extends from the outlet port and past a bottom of the drive housing, the method further comprising forming a sealed engagement against a tool driver of a robotic manipulator with the skirt when the drive housing is removably attached to the tool driver. Element 17: further comprising introducing a tool into the annulus through the proximal seal, and advancing the tool distally to the distal seal within the annulus.

By way of non-limiting example, exemplary combinations applicable to A, B, and C include: Element 2 with Element 3; Element 3 with Element 4; Element 2 with Element 5; Element 5 with Element 6; Element 2 with Element 7; Element 2 with Element 8; and Element 14 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:

a drive housing;

a shaft extending distally from the drive housing;

a distal seal arranged at a distal end of the shaft;

a flush tube extending from the drive housing within the shaft and terminating proximal to the distal seal, wherein a flushing fluid conveyed distally through the flush tube is discharged from the flush tube and impinges upon the distal seal; and a proximal drain arranged within the drive housing and in fluid communication with an annulus defined between the flush tube and an inner wall of the shaft, wherein the flushing fluid discharged from the flush tube circulates proximally within the annulus to the proximal drain to be discharged from the drive housing.

2. The surgical tool of claim 1, further comprising:

an end effector operatively coupled to the distal end of the shaft; and a wrist interposing the end effector and the distal end of the shaft, wherein the distal seal is mounted to the wrist.

3. The surgical tool of claim 1, wherein the proximal drain includes:

an upper housing in fluid communication with the annulus; and an outlet port extending from the upper housing.

4. The surgical tool of claim 3, wherein the shaft is operatively coupled to the upper housing within the drive housing.

5. The surgical tool of claim 4, wherein a driven gear is mounted to the shaft within the drive housing, and a proximal end of the driven gear extends into an interior of the upper housing and thereby operatively couples the shaft to the upper housing.

6. The surgical tool of claim 3, wherein the upper housing defines:

a housing central aperture sized to receive the flush tube extending through the upper housing; and a plurality of housing cable apertures sized to receive a corresponding plurality of drive cables extending from the drive housing and through the distal seal.

7. The surgical tool of claim 6, further comprising a drain sleeve received within the upper housing and providing:

a sleeve central aperture coaxially alignable with the housing central aperture to receive the flush tube;

a plurality of sleeve cable apertures coaxially alignable with the plurality of housing cable apertures; and a drain aperture alignable with the outlet port to allow the flushing fluid entering the proximal drain to flow into the outlet port.

8. The surgical tool of claim 7, wherein each sleeve cable aperture exhibits a diameter smaller than a diameter of each housing cable aperture to sealingly engage an outer circumference of each drive cable.

9. The surgical tool of claim 3, wherein the proximal drain further includes a skirt extending from the outlet port and past a bottom of the drive housing.

10. A method of flushing a surgical tool, comprising:

conveying a flushing fluid into a flush tube arranged within a shaft extending distally from a drive housing of the surgical tool;

discharging the flushing fluid from the flush tube proximal to a distal seal arranged at a distal end of the shaft;

impinging the flushing fluid on the distal seal and portions of the shaft and thereby removing debris and bioburden from the distal seal;

circulating the flushing fluid back to the drive housing within an annulus defined between the flush tube and an inner wall of the shaft;

receiving the flushing fluid at a proximal drain arranged within the drive housing and in fluid communication with the annulus; and discharging the flushing fluid from the drive housing via the proximal drain.

11. The method of claim 10, wherein the proximal drain includes an upper housing in fluid communication with the annulus, and an outlet port extending from the upper housing, the upper housing defining a housing central aperture sized to receive the flush tube extending through the upper housing, and a plurality of housing cable apertures sized to receive a corresponding plurality of drive cables extending from the drive housing and through the distal seal, the method further comprising:

receiving the flushing fluid from the annulus at the upper housing; and discharging the flushing fluid from the proximal drain at the outlet port.

12. The method of claim 11, wherein a drain sleeve is received within the upper housing and provides a sleeve central aperture coaxially alignable with the housing central aperture to receive the flush tube, and a plurality of sleeve cable apertures coaxially alignable with the plurality of housing cable apertures, the method further comprising:

sealingly engaging an outer surface of the flush tube with the sleeve central aperture; and sealingly engaging an outer surface of each drive cable with the plurality of sleeve cable apertures.

13. The method of claim 10, wherein a skirt extends from the outlet port and past a bottom of the drive housing, the method further comprising forming a sealed engagement against a tool driver of a robotic manipulator with the skirt when the drive housing is removably attached to the tool driver.

14. The method of claim 10, further comprising:

introducing a tool into the annulus through the proximal seal; and advancing the tool distally to the distal seal within the annulus.

* * * * *